(12) United States Patent
Tseng et al.

(10) Patent No.: US 10,532,314 B2
(45) Date of Patent: Jan. 14, 2020

(54) WASTE-LIQUID PROCESSING DEVICE AND AN AIR-POLLUTION TREATMENT DEVICE USING THE SAME

(71) Applicants: Feng-Yuan Tseng, New Taipei (TW); Jiun-Hong Tseng, Kaohsiung (TW); Jui-Po Tseng, Kaohsiung (TW); Te-Hui Liu, Taitung County (TW); Te-Jung Liu, Taitung County (TW)

(72) Inventors: Jui-Po Tseng, Kaohsiung (TW); Feng-Yuan Tseng, New Taipei (TW); Jiun-Hong Tseng, Kaohsiung (TW)

(73) Assignees: Feng-Yuan Tseng, New Taipei (TW); Jiun-Hong Tseng, Kaohsiung (TW); Jui-Po Tseng, Kaohsiung (TW); Te-Hui Liu, Taitung, Taitung County (TW); Te-Jung Liu, Taitung, Taitung County (TW)

(*) Notice: Subject to any disclaimer, the term of this patent is extended or adjusted under 35 U.S.C. 154(b) by 296 days.

(21) Appl. No.: 15/604,147

(22) Filed: May 24, 2017

(65) Prior Publication Data
US 2017/0341021 A1    Nov. 30, 2017

(30) Foreign Application Priority Data

May 25, 2016   (TW) .............................. 105116327 A

(51) Int. Cl.
| | | |
|---|---|---|
| A61L 2/00 | (2006.01) | |
| C02F 1/68 | (2006.01) | |
| B01D 53/02 | (2006.01) | |
| B01D 53/78 | (2006.01) | |
| A61L 9/14 | (2006.01) | |
| B01D 53/34 | (2006.01) | |
| B01D 53/64 | (2006.01) | |
| B01D 53/96 | (2006.01) | |

(52) U.S. Cl.
CPC .............. *B01D 53/78* (2013.01); *A61L 9/145* (2013.01); *B01D 53/346* (2013.01); *B01D 53/64* (2013.01); *B01D 53/96* (2013.01); *A61L 2209/21* (2013.01); *B01D 2251/108* (2013.01); *B01D 2257/60* (2013.01); *B01D 2257/91* (2013.01)

(58) Field of Classification Search
CPC ......... A61L 2/0094; A61L 2/18; A01N 59/00; A61K 33/00; C02F 1/76; C02F 1/727
USPC ........ 422/292, 305; 210/749, 753, 754, 764, 210/263, 323.1, 348; 96/108, 134, 243
See application file for complete search history.

(56) References Cited

U.S. PATENT DOCUMENTS 4,334,968 A * 6/1982 Sweeney .............. C02F 1/46109
                                                  204/256
5,858,246 A * 1/1999 Rafter ..................... C02F 1/505
                                                  210/753

\* cited by examiner

*Primary Examiner* — Monzer R Chorbaji
(74) *Attorney, Agent, or Firm* — Muncy, Geissler, Olds & Lowe, P.C.

(57) ABSTRACT

The present invention provides a waste-liquid processing device, comprising: a first processing device and a mixing device, wherein the first processing device is provided with a first purifying unit for processing waste liquid from a waste liquid source to produce a purified liquid. The mixing device is used for mixing the purified liquid with a chlorine dioxide solution. The present invention also provides an air-pollution treatment device, comprising the waste-liquid processing device and a gas processing device. The gas processing device comprises an air extracting unit, a gas purifying unit, a gas-liquid separation unit, and an exhausting unit.

9 Claims, 3 Drawing Sheets

WASTE-LIQUID PROCESSING DEVICE AND AN AIR-POLLUTION TREATMENT DEVICE USING THE SAME

FIELD OF THE INVENTION

The present invention is related to a device using a food grade chlorine dioxide solution with high purity for processing the polluted air, and especially to a waste-liquid processing device using the chlorine dioxide solution, and an air-pollution treatment device using the same capable of sterilizing the microorganism completely without generation of new variants, and strongly oxidizing the chemical substance such as heavy metals, so as to improve performance of the existing air pollution treatment device and air cleaning device, and to reduce the waste of water resources by converting the waste liquid into a neutralized solution for using again.

BACKGROUND OF THE INVENTION

In recent years, the economy of Asian countries has grown significantly and is unstoppable. However, the cost to pay for the economic growth is very high. The damage caused by the endless discharge of polluted gas or air has led to declining of national economic growth. For example, the dust haze makes people so afraid and damages their health. Specifically, during the process of production of the refining industry, steel industry, power plants and the semiconductor industry, acidic and alkaline waste-gas will be produced. The acidic waste gas mainly contains sulfur oxides, nitrogen oxides, hydrogen sulfide, sulfur dioxide, nitrogen dioxide, carbon dioxide and so on while the alkaline waste-gas mainly contains gaseous ammonia and gaseous metal oxides produced at high temperature, such as potassium hydroxide, sodium hydroxide and volatile organic waste-gas. Gases such as sulfur dioxide, nitrogen dioxide and suspended particles would irritate the respiratory system of human body and cause discomfort, and high concentrations of such gases can cause heart and respiratory diseases. Carbon monoxide would combine with hemoglobin easily to form carboxyhemoglobin that is hard to decompose, and thus the ability of transporting oxygen is affected.

Currently, the treatment method for acidic and alkaline gas is generally by means of absorption, the principle of which is to absorb pollutants in the waste gas into washing liquid by the gas absorption process with two-phase contact (liquid-gas). The common washing device is a wet scrubber. For a washing device, the waste gas and the washing liquid are required to be in full contact, so as to improve the efficiency of the absorption. On the other hand, for processes of the semiconductor and optoelectronic, the wet scrubber is also mainly used for the treatment of acidic and alkaline gas. The washing device usually contains the packing with a very large surface area, and has the purpose of making gas and liquid to be fully contacted with each other. In practice, the waste gas to be treated flows into the scrubber through its bottom, and the washing liquid is sprayed into the scrubber from its top by a spraying device. After the washing liquid is in contact with the treated waste gas flowing upwardly and absorbs the gaseous solute (pollutants) of the waste gas on the way of the washing liquid flowing through the packing, the washing liquid is converted into a resulting waste liquid, and then the resulting waste liquid is outputted from the bottom of the scrubber.

However, the scrubber mentioned above would cause serious fouling problems. The accumulation of granular particles is mainly due to the precipitation of particulate pollutants carried in the waste gas and the crystallization from the chemical reaction such as the salt crystals formed from acid gas in the waste gas and so on. In addition, the components of the scrubber such as packing, pipelines, nozzles, and flow meters are often attached with the biofilm. If the waste gas contains volatile organic substances, the washing liquid contains too much nitrogen salts ($NO^{3-}$ or $NH^{4+}$ such as the one in an untreated groundwater), or the waste gas contains nitric acid or ammonia gas, it would provide carbon source for microbial to grow and make the growth of the biofilm more serious. Moreover, in order to prevent the problem of environmental pollution caused by the used waste liquid, it is a common practice in the art to use the used washing liquid again or to reuse the same secondarily (or several times), so as to reduce the total amount of produced waste water. However, it could make concentration of pollutants in above waste liquid increased significantly, resulting in the inconvenience of follow-up process.

Chlorine dioxide is the A1-level safe and efficient physical sterilization deodorant recommended unanimously by World Health Organization and the World Food Organization. By the strong oxidizing ability and effective sterilization of the Chlorine dioxide of the present invention, they prevent scaling deposition and corrosion of pipeline, and strongly oxidize heavy metals and chemical substance. Unlike the reaction mechanism of chlorine gas by the addition or substitution reaction with the reactants, chlorine dioxide is a strong oxidant, composed of one chlorine atom and two oxygen atoms, and combined with 19 electrons. There is an unpaired active free electron in the outermost electron orbital. A special single electron transfer mechanism permits selectivity, and chlorine dioxide attacks the organic molecules (treated object) when the outermost orbital of the organic molecules is full. Chlorine dioxide takes one of the electrons and become chlorite ions and releases oxygen atoms according to the principle of attraction and repulsion, so as to cause irreversible oxidation damage and decomposition. Chlorine dioxide decomposes protein, fat, and nucleic acid of micro-organisms through oxidation, so as to achieve the function of the deactivation, and the principle of which is to oxidize and decompose the amino acid of microorganisms, so as to achieve the deactivation of the diploid of higher animals or plant cells without harmful influence. Therefore, the purpose of disinfection and deodorization is achieved.

It is confirmed by research that chlorine dioxide can effectively destroy organic pollutants in water such as: benzopyrene, anthraquinone, anthracene, chloroform, carbon tetrachloride, phenol, chlorophenol, organic acid, aniline, formaldehyde, amines, thiols, thiourea, nitrophenol and organic sulfide without the occurrence of chlorination reaction. Chlorine dioxide can also oxidize inorganic substances such as iron, lead, manganese, arsenic, sodium, phosphorus, magnesium, calcium, chlorine, nickel, cadmium, chromium, cyanide, sulfide to form non-toxic salts. On the other hand, because the molecules of chlorine dioxide can penetrate the cell wall of bacteria, chlorine dioxide will produce chlorite ions and oxygen after oxidizing cell wall (polysaccharides), and the produced chlorite ions and oxygen would react with the biofilm, resulting that the biofilm begins to peel, which will not lead to drug resistance or the generation of variants of the microbes. Therefore, although chlorine dioxide is effective for removal of biofilm and pollutants. However, there is no device for treating air pollution with chlorine dioxide in the market.

Moreover, when the existing products of chlorine dioxide in the market is mixed with water to form a chlorine dioxide solution in which the water is solvent, because the water still would contain a small amount of heavy metals, microorganisms and ions, chlorine dioxide would react with these heavy metals, microorganisms and ions and so on first, consequently the efficiency of chlorine dioxide for decontamination is significantly reduced. Accordingly, the amount of chlorine dioxide required to achieve the desired effect is greatly increased. Accordingly, in order to improve above problems and effectively apply the chlorine dioxide solution to the air-pollution treatment, the present invention is developed.

SUMMARY OF THE INVENTION

The main object of the present invention is to provide a waste-liquid processing device using chlorine dioxide solution and an air-pollution treatment device using the waste-liquid processing device for waste gas (or polluted gas) treatment. The air-pollution treatment device of the present invention is capable of recycling the waste liquid produced in the treatment and treating the recycled waste liquid while neutralizing the pH value of the same and converting it into a neutralized solution for reuse, thereby remarkably improving the performance of current air pollution treatment (for example, the treating effect for dusty haze) and air cleaning device, so as to effectively solve the technical problem in prior art such as accumulation of waste over time. On the other hand, the present invention also makes it effective for the chlorine dioxide solution of the present invention itself to be reacted only with pollutant rather than impurity in the water in a way of strongly oxidizing, sterilizing and deodorizing with full performance, thereby the using amount of the chlorine dioxide solution is greatly reduced while the overall effectiveness of the waste-liquid processing device and the air pollution treatment device in the art are maintained.

In order to fulfill above object, the present invention provides a waste-liquid processing device, comprising: a first processing device, provided with a first purifying unit for processing waste liquid from a waste liquid source to produce a purified liquid; and a mixing device, for mixing the purified liquid with a chlorine dioxide solution.

In implementation, the mixing device further comprises a first flow control unit, a processing unit, and a supply unit, wherein the supply unit is used for supplying a chlorine dioxide solution to the processing unit; the first flow control unit is adapted to control a flow rate and a flow amount of the chlorine dioxide solution flowing from the supply unit to the processing unit; and the processing unit is used for mixing the chlorine dioxide solution with the purified liquid from the first processing device to produce a liquid mixture. In implementation, the chlorine dioxide solution provided by the supply unit is produced by mixing purified water and gaseous chlorine dioxide. In implementation, the water reservoir is connected with the first processing unit to supply water to be mixed with the waste liquid.

In another embodiment, the first purifying unit is made by at least one of aluminium oxide ceramic, titania ceramic, zirconia ceramic, and carbon nanotube.

In another embodiment, the present invention provides an air-pollution treatment device, comprising: the waste-liquid processing device; and a gas processing device, comprising: an air extracting unit, for extracting gas; an gas purifying unit, connected with the air extracting unit and the waste-liquid processing device respectively, for processing the gas from the air extracting unit with the liquid mixture from the waste-liquid processing device, so as to produce a gas-liquid mixture; a gas-liquid separation unit, for separating the gas-liquid mixture from the gas purifying unit into a waste liquid and a purified gas; an exhausting unit for exhausting the purified gas.

In implementation, the waste liquid forms the waste liquid source from which the waste liquid is processed by the first processing device. In implementation, further comprising a processing device, provided between the waste-liquid processing device and the air-pollution treatment device, wherein the processing device comprises:
a second processing device, provided with at least one second purifying unit for processing the waste liquid to produce a purified liquid, and each of the at least one second purifying unit is made by at least one of aluminium oxide ceramic, titania ceramic, zirconia ceramic, and carbon nanotube; a sensing unit, for sensing a pH value of the purified liquid; an acid-base neutralization unit, for neutralizing the purified liquid according to the pH value sensed by the sensing unit, so as to produce a neutralized solution, and then the neutralized solution is supplied to the first processing unit. In implementation, further comprising a second flow control unit, wherein the second flow control unit is adapted to control a flow rate and a flow amount of the liquid mixture flowing from the waste-liquid processing device to the air-pollution treatment device.

In another embodiment, the second processing device includes a plurality of the second purifying units arranged in series, in parallel, or partly in series and partly in parallel.

The present invention will be understood more fully by reference to the detailed description of the drawings and the preferred embodiments below.

DETAILED DESCRIPTIONS OF PREFERRED EMBODIMENTS

Figure 1:
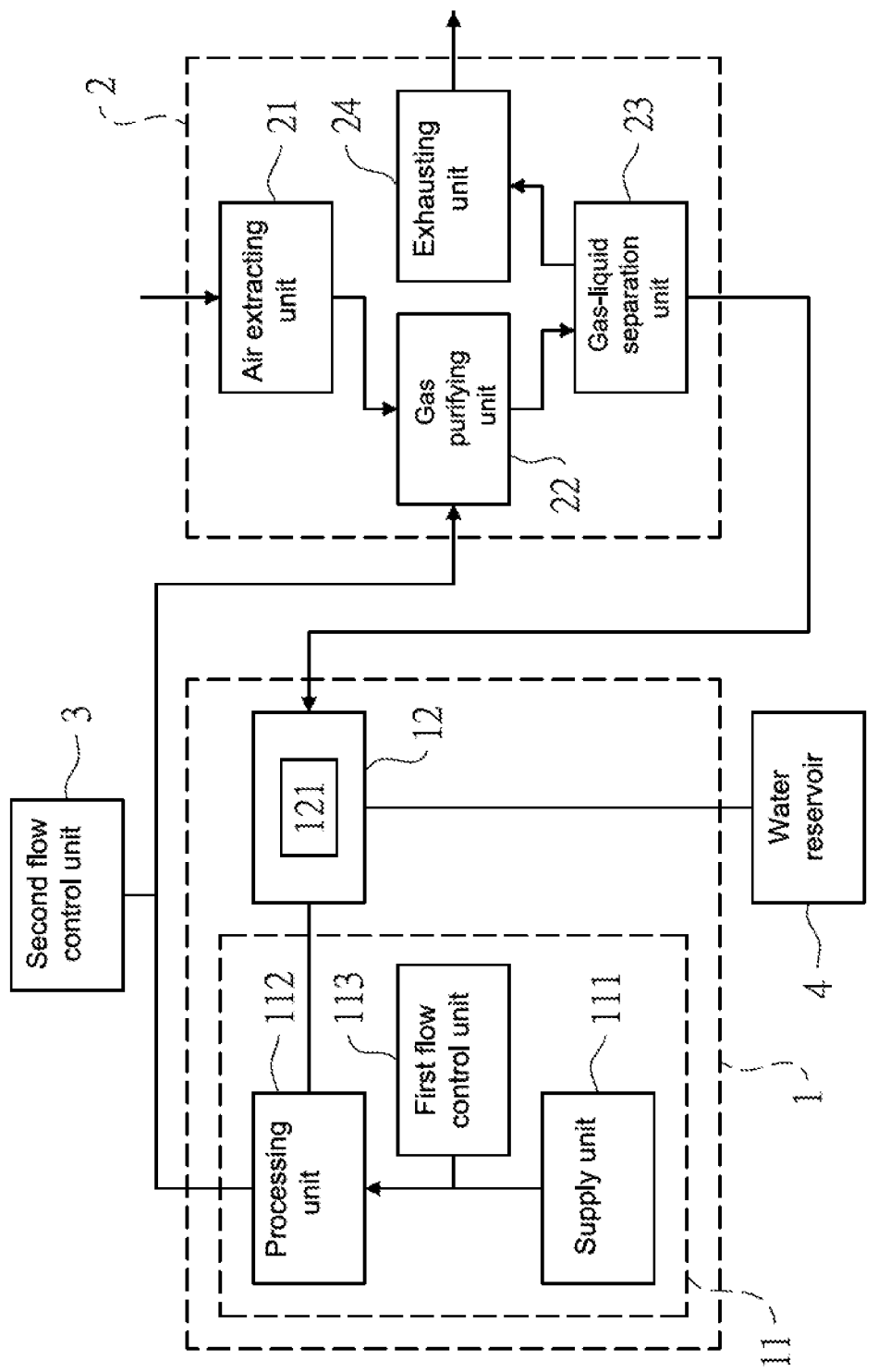
FIG. 1 is a schematic view showing an embodiment of the waste-liquid processing device and the air-pollution treatment device using the same in the present invention.

Referring to FIG. 1, the embodiment of the waste-liquid processing device 1 of the present invention comprises a mixing device 11, a first processing device 12, wherein the mixing device 11 includes a supply unit 111, a processing unit 112, and a first flow control unit 113. The embodiment of the air-pollution treatment device of the present invention comprises the waste liquid processing devices 1, a gas processing device 2, and a second flow control unit 3.

The operation of the waste liquid processing device 1 is described as follows. First, the first processing device 12 processes a waste liquid from a waste liquid source and produces a purified liquid. In above process, the pollutants such as heavy metals, microorganisms, ions and impurities in the waste liquid are removed by means of breaking molecular chains, changing the molecular cluster structure into small molecules, and most of bacteria and heavy metals are removed, and the waste liquid is purified. The first processing device 12 includes a first purifying unit 121 for destroying the molecular chain of the waste liquid. In another embodiment, a plurality of the first purifying units 121 may be connected in series or in parallel. The plurality of the first purifying units 121 are connected in series in order to enhance the effectiveness of these purifying units for processing the waste liquid having a lot of pollutants. A plurality of the first purifying units 121 are connected in parallel in order to process a large amount of waste liquid when it is required to process a large amount of waste liquid at the same time in the condition that the effectiveness of the plurality of the first purifying units 121 is the same, so as to increase the processing amount of waste liquid of the present invention. Moreover, the effectiveness of such processing can also be adjusted according to the need of users. Moreover, the first purifying unit 121 is made by at least one of aluminium oxide ceramic, titania ceramic, zirconia ceramic, and carbon nanotube. The impurities of titania ceramic, zirconia ceramic and aluminium oxide are removed by high-temperature calcinations, so as to produce micro-pores having connections therebetween. The carbon nanotube is made by graphite calcining at 3000° C. and has helical circulation. Aluminium oxide ceramic, titania ceramic, zirconia ceramic, and carbon nanotube can emit far infrared ray of $10^{12}$ to $10^{14}$ HZ/sec, and consequently, the water molecules of pure water passing through the combinations of above materials can be cut or processed by means of resonance, filtration, ion exchange and so on. The purified liquid is supplied to the processing unit 112 for processing and to be mixed with a chlorine dioxide solution.

The supply unit 111 is used to supply the food grade chlorine dioxide solution (chlorine dioxide solution used in the present invention may also be a common chlorine dioxide solution, but the effectiveness of which is not as good as the food grade chlorine dioxide solution of the present invention). The supply unit 111 is provided in a temperature-controlled chamber or in a dark room without sunlight at 11° C. or less than 11° C. since the boiling point of chlorine dioxide is 11 □, and the chlorine dioxide solution is obtained by mixing gaseous chlorine dioxide with water. The supply unit 111 is used for providing the chlorine dioxide solution and its concentration can be predetermined by users. The concentration of the food grade chlorine dioxide solution with high purity of the present invention is 3000 ppm and the percentage of chlorine of which is between 2% to 4% (gasification temperature of chlorine is 34° C.); the concentration of chlorine dioxide is between 96% to 98% and the food grade chlorine dioxide solution with high purity of the present invention does not contain chlorate, chlorite, hydrogen peroxide ($H_2O_2$) and other carcinogens or pollutants, so as to avoid the aforementioned carcinogens or pollutants being the pollution source. The general chlorine dioxide gas can also be used as solute in the present invention. The concentration of the chlorine dioxide solution of the present invention may be adjusted by setting proportionally the flow rate and the flow amount of the first flow control unit 113 in accordance with the concentration of pollutant in the purified liquid and user's requirements. In addition, it is necessary to further explain that the water (solvent) used in the chlorine dioxide solution of the present invention is produced by mixing the purified water and gaseous chlorine dioxide. In other words, impurities in the purified water obtained by processing tap water or groundwater such as heavy metals, microorganisms, other ions and others are decreased to minimum, so as to allow the best decontamination effect of the gaseous chlorine dioxide (solute).

Next, the chlorine dioxide solution supplied from the supply unit 111 is supplied to the processing unit 112 by the first flow control unit 113 with the flow rate and the flow amount set by the user according to the kinds of the pollutant, wherein the first flow control unit 113 is a common extraction and exhaustion device such as a dosing pump, thereby the chlorine dioxide solution is extracted at a set flow rate and flow amount. At this time, the processing unit 112 also receives the purified liquid from the first processing device 12, in which the chlorine dioxide solution is drawn by a venture tube, and the purified liquid is processed in a physical manner such as stirring, mixing and so on by the pressure generated by a pump (not shown), whereby the chlorine dioxide solution purifies the purified liquid to form a liquid mixture, and then the liquid mixture is supplied to an gas purifying unit 22 of the gas processing device 2. It is to be noted that the reason why the purified liquid needs to be purified by the chlorine dioxide solution is that the concentration of pollutants of the purified liquid can be reduced more effectively, so that the purified liquid can be used again rather than only used for the conventional precipitation treatment (such as chemical treatment and so on), such conventional treatment would result in that the concentration of waste is gradually increased. Moreover, the way that the purified liquid is purified by the chlorine dioxide solution would effectively reduce the waste of water resource in above process of the present invention. Moreover, since the majority of the molecular chains of the pollutant in the waste liquid is broken by the first processing device 12, the structure of the waste liquid is destroyed, whereby the chlorine dioxide solution can more easily oxidize the rest pollutants in the waste liquid that its structure is partly or overall broken. Moreover, the first processing device 12 can also be connected with a water reservoir 4 to provide tap water or groundwater for diluting and mixing the waste liquid, so the processing efficiency of the first processing device 12 becomes better. In addition, it should be noted that the waste-liquid processing device 1 of the present invention can be used independently for wastewater treatment in various industries.

The gas processing device 2 is used for treating gas produced in a power plant, an incinerator, a semiconductor factory, a coal plant, a refinery, a chemical raw material plant, a steelmaking field, a plastic factory and so on, specifically used in a packed bed scrubber, wet scrubbers, packed tower and various wet scrubbing systems. The gas processing devices 2 comprises an air extracting unit 21 for extracting gas, an gas purifying unit 22 connected with the air extracting unit 21 and the waste-liquid processing device 1 respectively for processing the gas from the air extracting unit 21 with the liquid mixture from the waste-liquid processing device 1, a gas-liquid separation unit 23, and an exhausting unit 24 for exhausting the purified gas. Other common device in wet scrubbing systems such as cooling devices, cooling towers, various pumps, air feeders . . . etc, could be included in the gas processing device 2 and are not described in detail. The gas purifying unit 22 processes the pollutants (chemical substance like heavy metals) in the gas from the air extracting unit 21 by mixing the gas with the liquid mixture and the chlorine dioxide solution with a strong purifying capacity in the liquid mixture as described above, so a gas-liquid mixture is formed and the chemical bond of the pollutants in the gas-liquid mixture are strongly oxidized by the chlorine dioxide solution, which makes chlorine dioxide more easily attract the small molecules in a way of attraction, so as to form small molecules while the microorganisms in the gas-liquid mixture are inactivated. In other words, the extracting gas is purified by means of strong oxidation while being processed into small molecules, thus the proportion of pollutants is reduced to minimum, and the air-pollution treatment device of the present invention with such technical effect can even replace the packing in the prior art. Thereafter, the gas-liquid separation unit 23 separates the gas-liquid mixture coming from the gas purifying unit 22 into a waste liquid and a purified gas. The gas-liquid mixture produced during the treatment of the gas purifying unit 22 is separated into the waste liquid and the purified gas by the gas-liquid separation unit 23, wherein the waste liquid is supplied to the first processing device 12 of the waste-liquid processing device 1, and the purified gas is exhausted by the exhausting unit 24, thus one-cycle process of the air-pollution treatment device of the present invention is completed. The exhausting unit 24 may further include a windmill, a motor-driven exhausting device and so on, which are not described here. Moreover, the second purifying unit 3 is provided between the waste-liquid processing device 1 and the air-pollution treatment device 2, so as to control a flow rate and a flow amount of the liquid mixture flowing from the waste-liquid processing device 1 to the air-pollution treatment device 2.

Figure 2:
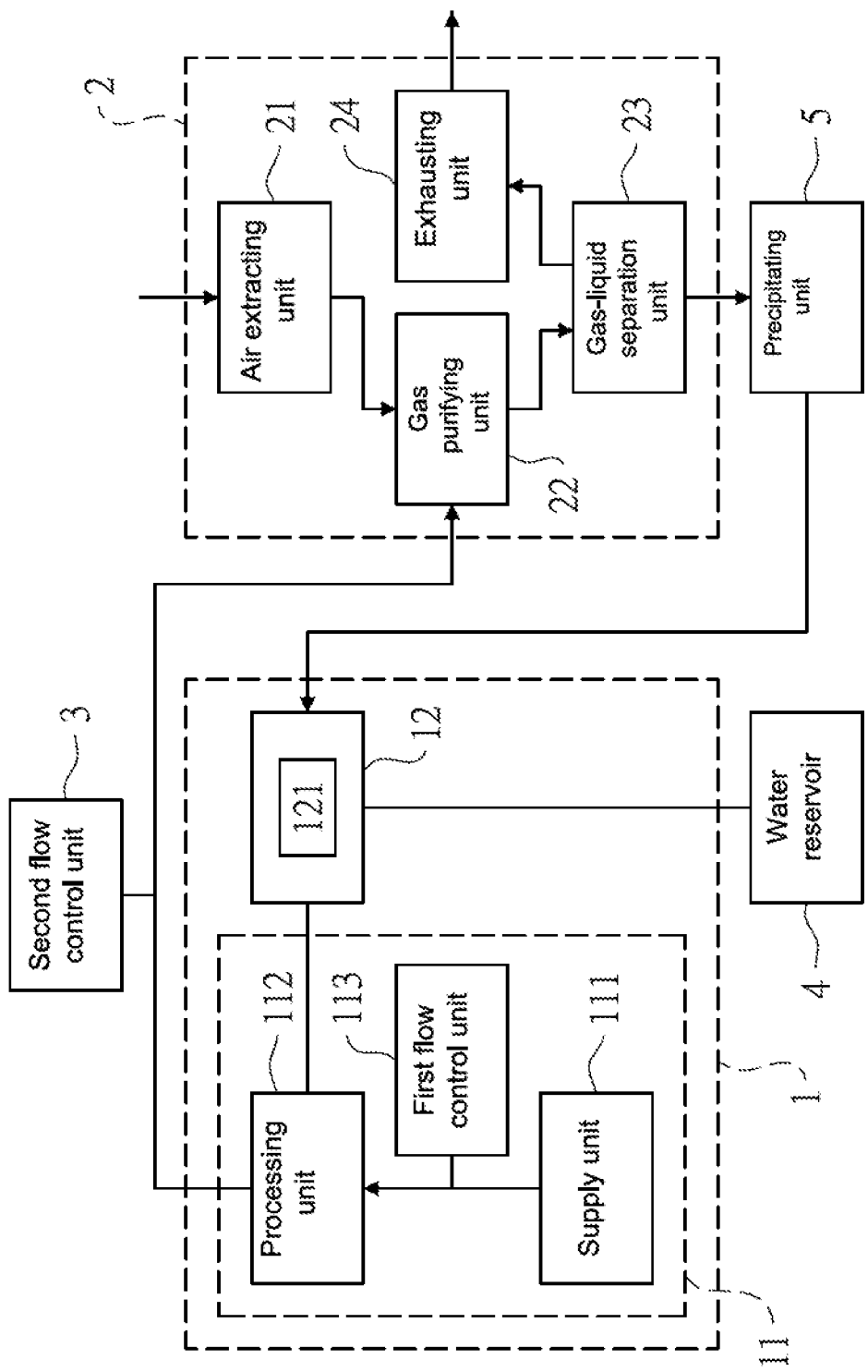
FIG. 2 is a schematic view showing another embodiment of the waste-liquid processing device and the air-pollution treatment device using the same in the present invention.

Referring to the embodiment of the present invention in FIG. 2, it is different from the first one as shown in FIG. 1 in that a precipitating unit 5 is provided between the gas-liquid separation unit 23 and the first processing device 12 for precipitating the waste liquid produced by the gas-liquid separation unit 23 in a way of chemical treatment by adding a chemical substance commonly used or physical treatment such as filtration, disinfection, decolorization, deodorization, exposure, and so on. In the precipitating unit 5, the residual liquid of the waste liquid after being precipitated is supplied to the first processing device 12 to be processed. In other words, the precipitating unit 5 may be regarded as another waste liquid source. As described above, The first processing device 12 processes the residual liquid of the waste liquid after being precipitated to produce another purified liquid, and the pollutants such as heavy metals, microorganisms, ions and the like in the residual liquid of the waste liquid after being precipitated is purified during the above process, so to produce another purified liquid (or another residual liquid).

Thereafter, the chlorine dioxide solution from the supply unit 111 will further purify above another purified liquid in the processing unit 112. Then, after above another purified liquid is processed with the chlorine dioxide solution, the resulting liquid mixture is supplied to gas purifying unit 22, and the above process is repeated as described above. Therefore, the present invention can effectively reduce concentration of the pollutant and microbe of the waste liquid treated by the air-pollution treatment device 2, and the waste liquid can be used again, regardless of whether the waste liquid is precipitated by the precipitating unit 5 or not, so as to effectively reduce the water and power consumption of the waste-liquid processing device 1, the air-pollution treatment device 2 and the precipitating unit 5, and also to effectively reduce the consumption of the chlorine dioxide solution in the subsequent processes.

Figure 3:
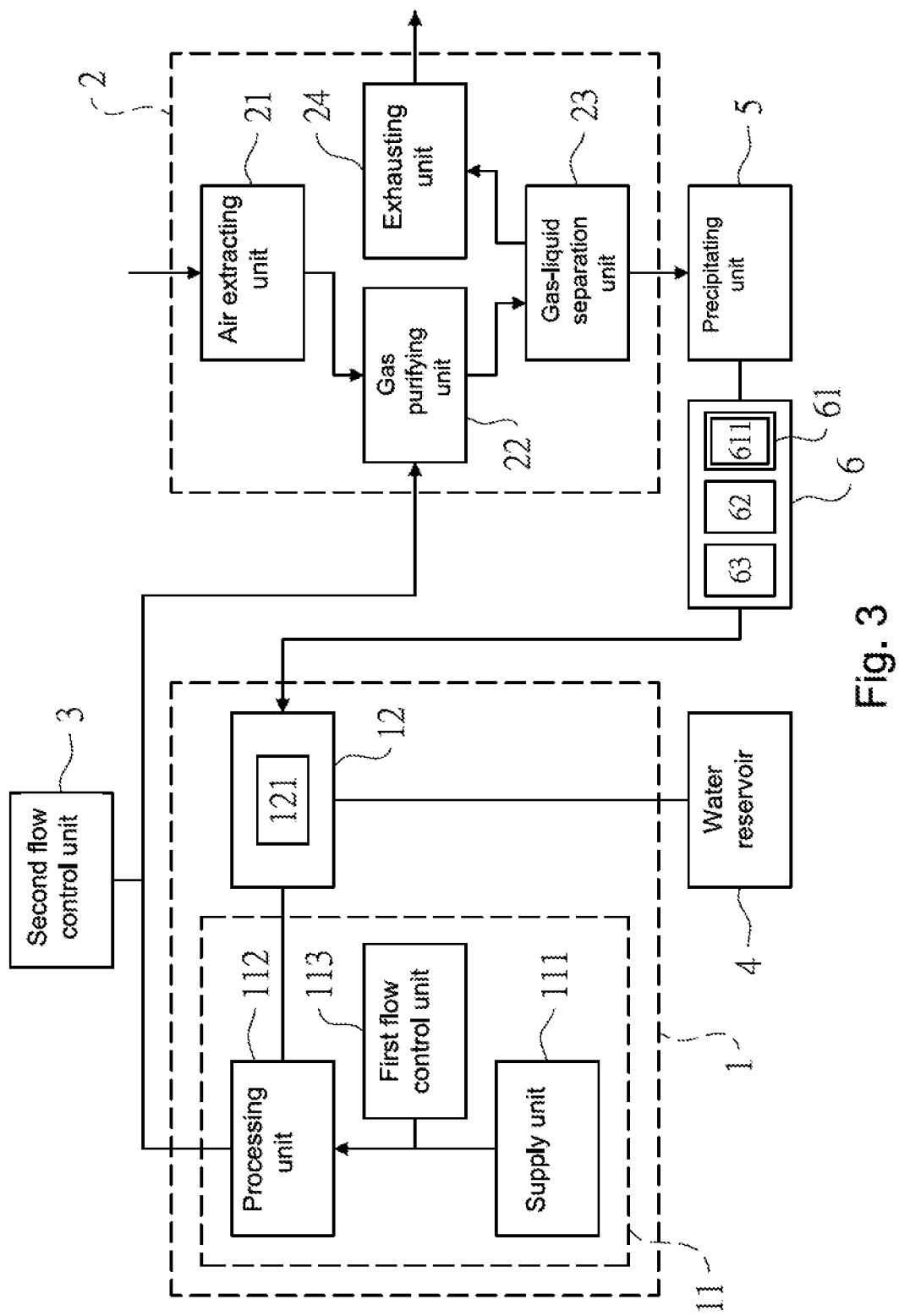
FIG. 3 is a schematic view showing another embodiment of the waste-liquid processing device and the air-pollution treatment device using the same in the present invention.

Referring to FIG. 3, it is difference from first one in FIG. 1 and second one in FIG. 2 in that a processing device 6 is provided between the waste-liquid processing device 1 and the air-pollution treatment device 2, wherein the processing device 6 is provided with a second processing device 61 for processing the waste liquid to produce another purified liquid. Similarly, the purpose of such configuration is to break the chemical bonds of the resulting waste liquid from the air-pollution treatment device 2 or from the precipitating unit 5 to be broken into the resulting waste liquid with small molecule, so as to improve the performance of chlorine dioxide solution used in the subsequent process. Moreover, the second processing device 61 is provided with at least one second purifying unit 611 for processing the resulting waste liquid, and the molecular chain of the same is destroyed, so as to produce a purified liquid, wherein each of the at least one second purifying unit is made by at least one of aluminium oxide ceramic, titania ceramic, zirconia ceramic, and carbon nanotube. Similarly, the performance of the second purifying unit 611 may be adjusted in accordance with the need of the user. A plurality of the second purifying units may be arranged in series, in parallel, or partly in series and partly in parallel. The performance of plurality of the second purifying unit 611 can be increased when in series, so as to make it able to process pollutants with high concentration of chemical substance. The plurality of the second purifying unit 611 arranged in parallel can simultaneously process a large amount of the waste liquid, together with the combination of the above various materials set by the second purifying unit 611, so as to achieve the optimum technical effect. Thereafter, the pH value of the purified liquid is sensed by a sensing unit 62. And, an acid-base neutralization unit 63 neutralizes the purified liquid according to the pH value sensed by the sensing unit 62. For example, if the purified liquid is alkaline, it is treated in a specific acidic chemical environment; if the purified liquid is acidic, it is treated in a specific alkaline chemical environment, so as to produce a neutralized solution, and then the neutralized solution is supplied to the first processing unit 12 to be processed with the steps as described above. In this way, the waste liquid is further processed by the processing device 6, so the waste liquid becomes a neutralized solution. Therefore, such process can improve the efficiency of the chlorine dioxide solution used in the subsequent step.

Thus, the present invention has the following advantages:
1. The waste liquid after being precipitated is processed by the first processing device 12 or the second processing device 61, so as to effectively reduce the concentration of the pollutants therein and the consumption of the water resource.
2. The waste liquid treated by the air-pollution treatment device 2 is repeatedly purified by the food grade chlorine dioxide solution with high-efficiency purification capability and with high purity. The cooperation of the air-pollution treatment device 2, the first processing device 12, and the processing device 6 could effectively solve the problem that the accumulated concentration of the waste over time in the prior art.
3. The water required for chlorine dioxide solution is pre-processed, and the molecular chains of the impurity or possible pollutant in the water are broken, and the water is reduced to small molecule and is sterilized, and consequently the chlorine dioxide solution itself could react with pollutants, so as to perform more strong oxidation and sterilization, and to significantly reduce the amount of chlorine dioxide solution to be used (because chlorine dioxide of chlorine dioxide solution can oxidize the pollutants themselves). Moreover, the overall performance of known waste-liquid processing device and air-pollution treatment device in the art are enhanced.

The description referred to in the drawings and stated above is only for the preferred embodiments of the present invention. Many equivalent variations and modifications can still be made by those skilled at the field related with the present invention and do not depart from the spirit of the present invention, so they should be regarded to fall into the scope defined by the appended claims.

To sum up, the waste-liquid processing device and the air-pollution treatment device using the same provided by the present invention can indeed meet its anticipated object, and they can be applied to the currently available waste-liquid processing device and air-pollution treatment device easily.

What is claimed is:

1. An air-pollution treatment device, comprising:
   a waste-liquid processing device, comprising:
      a first processing device, provided with a first purifying unit for processing waste liquid from a waste liquid source to produce a purified liquid; and
      a mixing device, for mixing the purified liquid with a chlorine dioxide solution;
   a gas processing device, comprising:
   an air extracting unit, for extracting gas;
   a gas purifying unit, connected with the air extracting unit and the waste-liquid processing device respectively, for processing the gas from the air extracting unit with the liquid mixture from the waste-liquid processing device, so as to produce a gas-liquid mixture;
   a gas-liquid separation unit, for separating the gas-liquid mixture from the gas purifying unit into a waste liquid and a purified gas; and
   an exhausting unit for exhausting the purified gas.

2. The air-pollution treatment device according to claim 1, wherein the waste liquid forms the waste liquid source from which the waste liquid is processed by the first processing device.

3. The air-pollution treatment device according to claim 1, further comprising a processing device, provided between the waste-liquid processing device and the air-pollution treatment device, wherein the processing device comprises:
   a second processing device, provided with at least one second purifying unit for processing the waste liquid to produce a purified liquid, and each of the at least one second purifying unit is made by at least one of aluminium oxide ceramic, titania ceramic, zirconia ceramic, and carbon nanotube;
   a sensing unit, for sensing a pH value of the purified liquid;
   an acid-base neutralization unit, for neutralizing the purified liquid according to the pH value sensed by the sensing unit, so as to produce a neutralized solution, and then the neutralized solution is supplied to the first processing unit.

4. The air-pollution treatment device according to claim 3, wherein the second processing device includes a plurality of the second purifying units arranged in series, in parallel, or partly in series and partly in parallel.

5. The air-pollution treatment device according to claim 1, further comprising a second flow control unit, wherein the second flow control unit is adapted to control a flow rate and a flow amount of the liquid mixture flowing from the waste-liquid processing device to the air-pollution treatment device.

6. The air-pollution treatment device according to claim 1, wherein the mixing device further comprises a first flow control unit, a processing unit, and a supply unit, wherein the supply unit is used for supplying a chlorine dioxide solution to the processing unit; the first flow control unit is adapted to control a flow rate and a flow amount of the chlorine dioxide solution flowing from the supply unit to the processing unit; and the processing unit is used for mixing the chlorine dioxide solution with the purified liquid from the first processing device to produce a liquid mixture.

7. The air-pollution treatment device according to claim 6, wherein the chlorine dioxide solution provided by the supply unit is produced by mixing purified water and gaseous chlorine dioxide.

8. The air-pollution treatment device according to claim 1, further comprising a water reservoir, wherein the water reservoir is connected with the first processing unit to supply water to be mixed with the waste liquid.

9. The air-pollution treatment device according to claim 1, wherein the first purifying unit is made by at least one of aluminium oxide ceramic, titania ceramic, zirconia ceramic, and carbon nanotube.

* * * * *